(12) United States Patent
Llewellyn

(10) Patent No.: US 6,531,162 B1
(45) Date of Patent: Mar. 11, 2003

(54) ADRENERGICALLY-MEDIATED WEIGHT LOSS PRODUCT

(76) Inventor: William Charles Llewellyn, P.O. Box 1162, Sound Beach, NY (US) 11789

(*) Notice: Subject to any disclaimer, the term of this patent is extended or adjusted under 35 U.S.C. 154(b) by 0 days.

(21) Appl. No.: 10/208,493

(22) Filed: Jul. 30, 2002

(51) Int. Cl.⁷ .................................................. H61K 35/78
(52) U.S. Cl. ........................ 424/729; 514/763; 514/764
(58) Field of Search .......................... 424/729; 514/763, 514/764

(56) References Cited

U.S. PATENT DOCUMENTS 4,613,672 A * 9/1986 Hara et al.
6,143,746 A * 11/2000 Daugan et al.

FOREIGN PATENT DOCUMENTS

JP 11-180869 A * 7/1999

OTHER PUBLICATIONS

Delbarre et al. Comp. Biochem. Physiol. C Comp. Pharmacol. (1982), vol. 72, No. 1, pp. 153–157.*
Dulloo et al. Am. J. Clin. Nutr. (1999), vol. 70, pp. 1040–1045.*
Dulloo et al. Int. J. of Obesity (2000), vol. 24, pp. 252–258.*

* cited by examiner

*Primary Examiner*—Leon B. Lankford, Jr.
*Assistant Examiner*—Susan D. Coe

(57) ABSTRACT

This invention discloses a new and unique combination of octopamine, yohimbine, bergenin and decaffeinated green tea extract useful as an oral supplement for increasing weight loss in humans.

2 Claims, No Drawings

ADRENERGICALLY-MEDIATED WEIGHT LOSS PRODUCT

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

Prior art relating to this invention concerns distinct areas previously not combined to create new and useful formula sets regarding a solid-dosage form of a weight loss product.

This invention relates a new and unique combination of octopamine, yohimbine, bergenin and decaffeinated green tea extract useful for increasing weight loss.

Octopamine is a naturally-occurring catecholamine structurally related to norephinephrine, and has been proven in in-vitro studies to be a potent selective beta-3 agonist (C R Acad Sci III 1993;316(5):519–23). Beta-3 receptors can be found in both human white and brown adipose tissues, and play an important role in lipolysis and thermogenesis in our bodies. They are vastly more important than previously thought by scientists, who often had difficulty in the past discerning the contribution of each beta-receptor subtype (1,2 and 3) without having agents selective for each to investigate. Various techniques were devised to try, but for a long time reports were not in favor of beta-3 receptors having much of a role in humans. It was not until a study conducted with ephedrine in 1995, however, that surprising new data started to arise in support of a beta-3-mediated pathway to fat loss. Using beta blocking agents investigators were able to demonstrate that beta-3 agonist activity likely accounted for at least 40% of the thermogenesis induced by this popular weight loss drug.

When a synthetic selective beta-3 agonist was finally developed and studied in humans in 2001, the important role of this receptor became an unquestionable fact (Clin Pharmacol Ther 2002;71:272–9). In this investigation a group of 12 otherwise healthy overweight men noticed a clear increase in lipolysis, as well as total energy expenditure, with the use of a beta-3 agonist exclusively. We are sure the intended action of the drug was solely responsible for these effects because heart-rate and diastolic blood pressure did not increase in any of the subjects (signs that non-selective beta agonistic activity were occurring), nor did the concentrations of the endogenous adrenergic hormones epinephrine and norepinephrine. Leptin, a hormone often relevant to weight loss, also did not change during the study. We are left with proof that beta-3 receptors are important triggers of lipolysis and thermogenesis in humans, and have opened a new door to weight loss without the uncomfortable jitters and central nervous system stimulation noted with non-selective beta agonists like ephedrine (selective beta-3 agonists do not produce the same strong CNS stimulation).

Yohimbine is an extremely potent naturally-occurring alpha-2 receptor antagonist. Adrenergic lipolysis in human adipose tissue is regulated in a dual nature by adrenoceptors. Most notably, activation of the beta-2 or beta-3 subtype increases the process of lipolysis; while activation of alpha-2 receptors diminishes it (fat cells appear to be the only type of cells in the human body that exhibit such dual regulation by adrenoceptors). Studies with yohimbine, in the form of yohimbine HCL, have shown that it is capable of increasing lipolysis in humans after oral dosing, likely via both alpha-2 receptor antagonism and increases in synaptic norephinephrine release (Eur J Clin Invest 1988;18:587–94). In effect it serves both beta stimulating and alpha blocking properties, an ideal combination if we want to stimulate fat loss. However, when single doses as high as 21.6 mg (J Clin Pharmacol 1996;36:814–22), or daily cumulative doses as high as 43.2 mg (J Urol 1995;141:1360–63), were taken, the agent was well tolerated, and had no significant impact on blood pressure or heart rate as would be expected of a beta-agonist like ephedrine.

Green tea leaf (camellia sinensis) extract has been around for centuries, and has been used in herbal medicine for about as long. Early on its beneficial properties were noticed, particularly in Asian cultures where Green Tea has been widely consumed and often thought of as a having numerous positive health benefits. In recent years scientists have been investigating the content and actions of Green Tea, and are coming to confirm with solid evidence many of its positive effects including those as an anti-oxidant, cholesterol lowering, antidepressant, capillary-strengthening and lipolysis-enhancing agent. Early suggestions were that its caffeine content was solely responsible for its ability to increase fat loss; however this was fundamentally dismissed in a study published in 1999 that demonstrated green tea to have an effect that could not be duplicated with an equivalent dose (50 mg) of caffeine (Int J Obesity 2000;24:252–58). In this investigation green tea increased 24 hour energy expenditure significantly, where the caffeine had no noticeable effect. It looks now like its high content of tea-catechins, particularly EGCG, which are the source of its activity here. Studies with Green Tea extract with standardized amounts of EGCG have suggested it exerts a direct effect on thermogenesis by increasing the respiration rate of brown fat cells, and furthermore that it can strongly enhance the lipolytic action of other chemicals or agents acting on this system (Am J Clin Nutr 1999;70:1040–5). In-vitro tea catechins like EGCG were shown to inhibit the COMT enzyme, which is responsible for degrading the adrenergic hormone norephinephrine (J Med Chem 1975;18:120–2). Since norepinephrine has an important role in human thermogenesis and fat metabolism, this likely accounts for much of its positive action here.

Bergenin comes from eastern herbal medicine originally, where it is found in the form of a plant extract called "Shengma". It is one of the now known active components of this plant extract, and has been shown to have an action in the body that augments the lipolytic action of norepinephrine. In-vitro studies have confirmed that while this compound itself does not directly stimulate lipolysis or have measurable adrenergic activity, but it markedly enhances lipolysis enduced by an adrenergic hormone such as norepinephrine (J. Nat Prod 1998;61:1006–11). It is further documented to oppose the lipogenic (fat building) actions of insulin. Its exact mode of action is unknown at this time, but it is believed to involve increased norepinephrine binding affinity to phosholipids on fat cells.

By triggering adrenergically-mediated lipolysis and thermogenesis with a carefully blended combination of octopamine and yohimbine, while simultaneously supporting the adrenergically-mediated activities of these compounds with a carefully blended composition of bergenin and decaffeinated green tea extract, this new product provides a unique and effective method for losing weight.

BRIEF SUMMARY OF THE INVENTION

Prior art relates many dietary supplement formulations for the purpose of increasing weight loss. Many, however, focus on the use of strong central nervous system stimulants such as caffeine and ephedrine (or its alkaloids). Although effective in many cases, stimulant-based weight loss products are often uncomfortable for many users due to the side effects related to their potential effects on the central nervous system, which may include restlessness, increased heart rate, sweating or insomnia. Prior art also discloses four compounds of interest to this inventor that are without strong stimulant properties, but which heretofore had not been combined to create a new and useful weight loss product. The problem of this invention was therefore to provide a new and unique composition for increasing weight loss in humans, but without the use of strong stimulants. According to this invention this problem is solved with a carefully blended composition containing octopamine, yohimbine, bergenin and decaffeinated green tea extract.

BRIEF DESCRIPTION OF THE SEVERAL VIEWS OF THE DRAWING

Not Applicable

DETAILED DESCRIPTION OF THE INVENTION

This invention discloses the formula sets that embody the invention of the supplement composition for increasing weight loss in humans. The combination of octopamine, yohimbine, bergenin and decaffeinated green tea extract increases lipolysis, thermogenesis and weight loss, and is safe and much less apt to cause the side effects normally associated with stimulant-based weight loss products.

We now discuss in detail the preferred versions, variants, or embodiments of this invention.

A representative formula for an oral Weight Loss Product is as follows, one tablet contains:

Octopamine 150 mg

Yohimbine 5 mg

Bergenin 100 mg

Decaffeinated Green Tea Extract (standardized for 60% EGCG content) 100 mg

Plus additional excipients:

A sufficient quantity of each to make a suitable tablet: dicalcium phosphate, magnesium stearate, silica, stearate, stearic acid, microcrystalline cellulose and croscarmellose sodium.

The scientific rationale for this formulation is as follows:

In the body adrenergic receptors closely mediate the disposition of fat stores. Stimulation of beta receptors sends a signal to release fatty acids from fat cells, and stimulating alpha receptors sends an opposite message, or to block the breakdown and release of fatty acids (Am J Clin Nutr 1992;55:228s–36s). Stimulation of beta receptors is a common focus for those looking for weight loss, as this subtype is directly responsible for triggering lipolysis. Many weight loss compositions focus on the use of ephedrine for example, which is a non-selective agonist of beta receptors. Its activity is strong as a lipolytic agent, being that it triggers lipolysis and thermogenesis through beta-2 and beta-3 receptors. It also has strong central nervous system effects through its activation of beta 1 and beta 2 receptors, and therefore can produce related side effects such as sweating, nervousness, insomnia, increased heart rate or restlessness. This invention therefore focuses on the use of a selective beta-3 agonist only. Studies with ephedrine have demonstrated that at least 40% of its thermogenic activity likely comes from beta-3 receptor agonist activities (Int J Obes Relat Metab Disord. 1995;19(9):678–85), so targeting this receptor specifically is an idea option to this inventor. Octopamine is an extremely potent naturally occurring beta-3 agonist, and studies have supported clearly that it is selective for this receptor in mammals.

Yohimbine is a potent naturally occurring alpha-2 receptor antagonist, and blocks the messaging system than negatively regulates lipolysis in human fat cells. It also strongly stimulates the synaptic release of norepinephrine, an endogenous beta-agonist extremely important to lipolysis. As such it serves a dual purpose, both by blocking alpha-2 activation and increasing the level of norepinephrine available to fat cells. Studies have furthermore shown that in reasonable doses it does not act as a strong central nervous system stimulant, so when used in direct accordance to this invention it should not be a strong instigator of stimulant-related side effects.

Decaffeinated green tea extract is included in this invention specifically for its EGCG content. Studies have shown that tea catechins such as EGCG inhibit the COMT enzyme in-vitro. The COMT enzyme is responsible for the degredation of norepinephrine, and EGCG can therefore increase the level of available norepinephrine available to fat cells by slowing down its removal from the body. It was included to work specifically with the other agents in this invention, so as to maximize stimulation of the adrenergic system without external stimulants.

Bergenin is an active constituent found in the dried rhizomes of the plant species thunbergii. Bergenin was shown in in-vitro studies to increase the lipolytic activity of norepinephrine. Its exact mode of action is unknown, but it is believed to increase norephinephrine binding to phospholipids in fat cells. As such it is an excellent synergistic addition to our composition. It itself exerts no direct adrenergic activity, as was elucidated in the study, but strongly bolsters the lipolytic action of norepinephrine, one of the bodies important adrenergic, lipolytic and thermogenic hormones and a large focus of this invention.

Without further elaboration, it is believed that one skilled in the art can, using the preceding description, utilize the present invention to its fullest extent. The specific formulas are included as the preferred embodiment of the composition formula ranges, and not to further qualify the description. Claim references to specific components include the component itself, as well as all concentrated, extracted, or purified forms of said ingredients.

I claim:

1. A weight loss method comprising administering a composition of matter comprising octopamine, yohimibine, bergenin, and decaffeinated green tea extract in amounts effective to promote weight loss.

2. A weight loss method comprising administering a composition of matter comprising octopamine, bergenin, and decaffeinated green tea extract in amounts effective to promote weight loss.

* * * * *